United States Patent
Fauchere et al.

(10) Patent No.: US 6,245,916 B1
(45) Date of Patent: Jun. 12, 2001

(54) AMINOTRIAZOLE COMPOUNDS

(75) Inventors: Jean-Luc Fauchere, Saint Cloud; Jean-Claude Ortuno, Versailles; Jacques Duhault, Saint-Lyphard; Jean Albert Boutin, Suresnes; Nigel Levens, Vaucresson, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/549,745

(22) Filed: Apr. 14, 2000

(30) Foreign Application Priority Data

Apr. 15, 1999 (FR) .................................. 99 04721

(51) Int. Cl.$^7$ .................................. C07D 249/12

(52) U.S. Cl. .................................. 548/263.8

(58) Field of Search .................................. 548/263.8

(56) References Cited

FOREIGN PATENT DOCUMENTS

99/32466 * 7/1999 (WO) .

* cited by examiner

*Primary Examiner*—Patricia L. Morris
(74) *Attorney, Agent, or Firm*—The Firm of Hueschen and Sage; G. Patrick Sage

(57) ABSTRACT

Compound of formula (I):

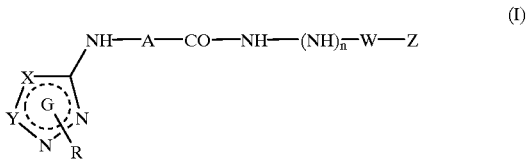

wherein:
  n is 0 or 1,
  W represents —CO— or $S(O)_q$ and q is 0, 1 or 2,
  G represents a $G_1$, $G_2$, $G_3$ or $G_4$ group as defined in the description,
  Z represents alkyl, aryl, heteroaryl, arylalkyl, arylalkenyl, arylalkynyl, heteroarylalkenyl, heteroarylalkynyl or heteroarylalkyl each optionally substituted.
  A represents a grouping selected from —$A_2$—, —$A_1$—$A_2$—, —$A_2$—$A_1$— and —$A_1$—$A_2$—$A_1$— wherein $A_1$ is alkylene and $A_2$ represents phenylene, cycloalkylene, naphthylene or heteroarylene each optionally substituted,
  R represents hydrogen, alkyl, aryl, heteroaryl, arylalkyl arylalkenyl, arylalkynyl, heteroarylakenyl, heteroarylalkynyl or heteroarylalkyl each optionally substituted,
  $R_1$ represents alkyl, aryl, heteroary, arylalkyl arylalkenyl, arylalkynyl, heteroarylalkenyl, heteroarylalkynyl or heteroarylalkyl each optionally substituted, and
medicinal products containing the same which are useful as Neuropeptide Y receptor ligands.

13 Claims, No Drawings

AMINOTRIAZOLE COMPOUNDS

The present invention relates to new aminotriazole compounds.

SUMMARY OF THE INVENTION

The compounds of the present invention have a novel structure characterised by the combination of an aminotriazole group, a hydrazide structure and an aromatic-type spacer. The compounds are used in the treatment of pathologies associated with the neuropeptide Y (NPY).

DESCRIPTION OF THE PRIOR ART

Various NPY receptor ligands have been described recently. By way of example, there may be mentioned cyclic peptide compounds (WO 9400486), amino acid compounds of arginine (WO 9417035) or non-peptide compounds (WO 9827063).

BACKGROUND OF THE INVENTION

The Neuropeptide Y (NPY) is a peptide of 36 amino acids, related to the peptide YY (PYY) and to pancreatic polypeptides (PP). Originally isolated from pig brain (Proc. Natl. Acad. Sci., 1982, 79, 5485), NPY is widely distributed in mammals at the level of the central and peripheral nervous systems. This neurotransmitter is present in high concentrations in nerve fibres of the brain, but also of the heart, the sympathetic ganglia, blood vessels and smooth muscles of the vas deferens and of the gastrointestinal tract. It is responsible for various physiological effects which are exerted via the intermediary of specific receptors (Y). The latter form a heterogeneous group, 6 sub-types of which have been identified to date: $Y_1$ to $Y_6$ (Pharmacological Reviews, 1998, 50, 143). NPY is involved in eating behaviour by strongly stimulating food intake (Proc. Natl. Acad. Sci., 1985, 82, 3940), or by exerting a regulatory role on the HPA (hypothalamic-pituitary-adrenal) axis (J. of Neuroendocrinol., 1995, 7, 273). It also exhibits anxiolytic and sedative properties (Neuropsychopharmacology, 1993, 8, 357), a strong vasoconstrictive ability (Eur. J. Pharmacol., 1984, 85, 519) which induces an increase in blood pressure, and also has an effect on the circadian rhythm (Neuroscience and Biobehavioral Reviews, 1995, 19, 349).

In addition to the fact that the compounds of the invention are new, they have demonstrated an in vivo inhibitory action on food intake and weight gain. That effect is exerted via the intermediary of binding to the NPY receptors. It will thus be possible to use the compounds of the invention in the treatment of pathologies in which an NPY receptor ligand is necessary, especially in the treatment of pathologies associated with eating behaviour disorders or energy balance disorders, such as diabetes, obesity, bulimia, anorexia nervosa, and also in the treatment of arterial hypertension, anxiety, depression, epilepsy sexual dysfunctions and sleep disorders.

DETAILED DESCRIPTION OF THE INVENTION

The present invention relates especially to compounds of formula (I):

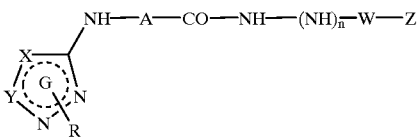

wherein
n is 0 or 1,
W represents a —CO— group or an $S(O)_q$ group wherein q is 0, 1 or 2,
the grouping

represents a group selected from:

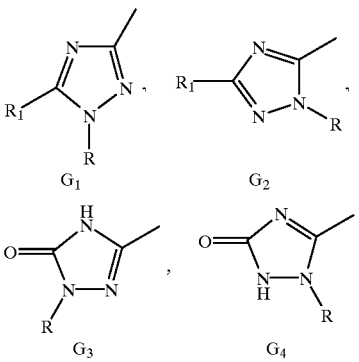

Z represents an alkyl, optionally substituted aryl, optionally substituted heteroaryl, optionally substituted arylalkyl, optionally substituted arylalkenyl, optionally substituted arylalkynyl, optionally substituted heteroarylalkenyl, optionally substituted heteroarylkynyl or optionally substituted heteroarylalkyl group, A represents a grouping selected from —$A_2$—, —$A_1$—$A_2$—, —$A_2$—$A_1$— and —$A_1$—$A_2$—$A_1$— wherein $A_1$ is an alkylene group and $A_2$ represents an optionally substituted phenylene, optionally substituted naphthylene, cycloalkylene, or optionally substituted heteroarylene group, R represents a hydrogen atom, or an alkyl, optionally substituted aryl, optionally substituted heteroaryl, optionally substituted arylalkyl, optionally substituted arylalkenyl, optionally substituted arylalkynyl, optionally substituted heteroarylalkenyl, optionally substituted heteroarylalkynyl or optionally substituted heteroarylalkyl group, $R_1$ represents an alkyl, optionally substituted aryl, optionally substituted heteroaryl, optionally substituted arylalkyl, optionally substituted arylalkenyl, optionally substituted arylalkynyl, optionally substituted heteroarylalkenyl, optionally substituted heteroarylkynyl or optionally substituted heteroarylalkyl group, their enantiomers, diastereoisomers, and addition salts thereof with a pharmaceutically acceptable acid or base, it being understood that
- the term "alkyl" denotes a linear or branched group having from 1 to 6 carbon atoms,
- the term "alkylene" denotes a linear or branched bivalent radical containing from 1 to 6 carbon atoms,
- the term alkenyl denotes a linear or branched group having from 2 to 6 carbon atoms and from 1 to 3 double bond,
- the term alkynyl denotes a linear or branched group having from 2 to 6 carbon atoms and from 1 to 3 triple bond,
- the term "aryl" denotes a phenyl, naphthyl, biphenyl, dihydronaphthyl or tetrahydronaphthyl group,
- the term "heteroaryl" denotes an unsaturated or partially unsaturated mono- or bi-cyclic group having from 5 to 11 ring members, containing from 1 to 4 hetero atoms selected from nitrogen, oxygen and sulphur,
- the terms "phenylene" and "naphthylene" denote bivalent phenyl and naphthyl radicals, respectively,
- the term cycloalkylene denotes a bivalent saturated cyclic radical having from 3 to 8 carbon atoms,
- the term "heteroarylene" denotes a bivalent heteroaryl radical as defined hereinbefore, the expression "optionally substituted" applied to the terms "aryl", "arylalkyl", "heteroaryl" or "heteroarylalkyl" means that those groups are substituted on their cyclic moiety by from 1 to 5 identical or different substituents selected from linear or branched ($C_1$–$C_6$)alkyl, linear or branched ($C_1$–$C_6$) alkoxy, halogen, hydroxy, linear or branched perhalo-($C_1$–$C_6$)alkyl, nitro, amino (optionally substituted by one or two linear or branched ($C_1$–$C_6$)alkyl groups), linear or branched ($C_1$–$C_6$)acyl, aminocarbonyl (optionally substituted on the nitrogen atom by one or two linear or branched ($C_1$–$C_6$)alkyl groups), linear or branched ($C_1$–$C_6$) acylamino, linear or branched ($C_1$–$C_6$)alkoxycarbonyl, formyl, carboxy, sulpho, nitrile, linear or branched ($C_1$–$C_6$) aminoalkyl (optionally substituted on the nitrogen atom by one or two linear or branched ($C_1$–$C_6$)alkyl group), linear or branched ($C_1$–$C_6$)thioalkyl (optionally substituted on the sulfur atom by a linear or branched ($C_1$–$C_6$)alkyl group), or linear or branched ($C_1$–$C_6$)hydroxyalkyl (optionally substituted on the oxygen atom by a linear or branched ($C_1$–$C_6$) alkyl group), the expression "optionally substituted" applied to the terms "phenylene", "naphthylene" or "heteroarylene" means that those groups are substituted by from one to three identical or different groups selected from linear or branched ($C_1$–$C_6$) alkyl, linear or branched ($C_1$–$C_6$)alkoxy, halogen, hydroxy, linear or branched perhalo-($C_1$–$C_6$)alkyl, nitro, amino (optionally substituted by one or two linear or branched ($C_1$–$C_6$)alkyl groups), linear or branched ($C_1$–$C_6$)acyl, formyl, carboxy, linear or branched ($C_1$–$C_6$)alkoxycarbonyl, aminocarbonyl (optionally substituted on the nitrogen atom by one or two linear or branched ($C_1$–$C_6$)alkyl groups), linear or branched ($C_1$–$C_6$)acylamino and nitrile.

Among the heteroaryl groups preference is given to the pyridyl, furyl, thienyl and indolyl groups.

Among the heteroarylene groups preference is given to the pyridinylene and pyrazinylene groups.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid. etc.

Among the pharmaceutically acceptable bases there may be mentioned by way of non-limiting example sodium hydroxide, potassium hydroxide, triethylamine, tert-butylamine, etc.

An advantageous aspect of the invention relates to compounds of formula (I) wherein n is 1.

Another advantageous aspect of the invention relates to compounds of formula (I) wherein n is 0.

Preferred compounds of the invention are those wherein W represents an $SO_2$ group.

Preferred compound s of the invention are those wherein the grouping

represents a group selected from:

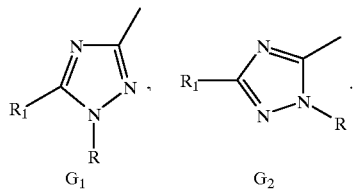

Other preferred compounds of the invention a re those wherein the grouping

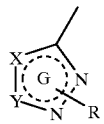

represents a group selected from:

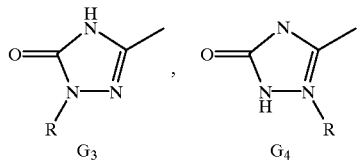

In preferred compounds of formula (I), A represents a grouping $A_2$, $A_2$ being more especially a phenylene, pyridinylene or pyrazinylene group.

In other preferred compounds of formula (I), A represents a grouping —$A_1$—$A_2$— or —$A_2$—$A_1$—$A_2$ being more especially a phenylene, pyridinylene or pyrazinylene group.

In the compounds of formula (I), $R_1$ preferably represents an optionally substituted aryl group.

In the compounds of formula (I), R will advantageously be selected from hydrogen, and an optionally substituted aryl group (more especially phenyl), and an optionally substituted heteroaryl group (more especially pyridinyl, furyl or thienyl).

An advantageous aspect of the invention relates to compounds of formula (I) wherein Z represents a group selected from alkyl, optionally substituted aryl and optionally substituted heteroaryl group.

The present invention relates especially advantageously to compounds of formula (I) wherein n is 1, W represents an $SO_2$ group, A represents a group selected from phenylene, pyridinylene and pyrazinylene, $R_1$ represents an optionally substituted aryl group, R is selected from a hydrogen atom, an optionally substituted aryl group and an optionally substituted heteroaryl group, and Z represents an alkyl, an optionally substituted aryl group or an optionally substituted heteroaryl group.

The preferred aryl group of the invention is the phenyl group.

The invention relates most especially to the following compounds:

N'-[4-({5-phenyl-1-[3-(trifluoromethyl)phenyl]-1H-1,2,4-triazol-3-yl}amino)benzoyl]benzenesulphonohydrazide 4-methoxy-N'-[4-({5-phenyl-1-[3-trifluoromethyl)phenyl]-1H-1,2,4-triazol-3-yl}amino)benzoyl]benzenesulphonohydrazide N'-{4-[(5-phenyl-1H-1,2,4-triazol-3-yl)amino]benzoyl}benzenesulphonohydrazide N'-(4-{[5-phenyl-1-(2-pyridyl)-1H-1,2,4-triazol-3-yl]amino}benzoyl)benzenesulphonohydrazide N'-[4-({5-oxo-1-[3-(trifluoromethyl)phenyl]-4,5-dihydro-1H-1,2,4-triazol-3-yl}amino)benzoyl}benzenesulphonohydrazide N'-(4-{[5-oxo-1-(2-pyridyl)-4,5-dihydro-1H-1,2,4-triazol-3-yl]amino}benzoyl)benzenesulphonohydrazide N'-[(6-{[5-oxo-1-(2-pyridinyl)-4,5-dihydro-1H-1,2,4-triazol-3-yl]amino}-3-pyridinyl) carbonyl]benzenesulphonohydrazide.

The present invention relates also to a process for the preparation of compounds of formula (I), characterised in that there is used as starting material a compound of formula (II):

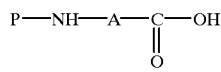

(II)

wherein A is as defined for formula (I) and P represents a protecting group for the amine function, which is reacted in the presence of a coupling agent with a compound of formula (III):

$NH_2$—$(NH)_n$—W—Z (III)

wherein n, W and Z are as defined for formula (I),
to yield, after deprotection of the amine function by removal of the P group, a compound of formula (IV):

(IV)

wherein n, A, W and Z are as defined hereinbefore,
which compound (IV) is then condensed in a basic medium with an isothiocyanate of formula (V):

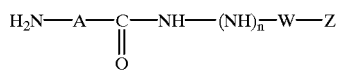

(V)

wherein R'₁ is as defined for R₁ in formula (I) or represents a linear or branched ($C_1$–$C_6$)alkoxy group, to yield a compound of formula (VI):

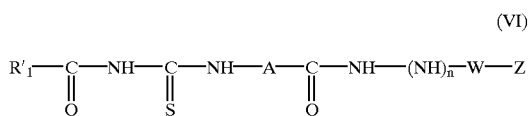

(VI)

wherein n, R'₁, A, W and Z are as defined hereinbefore.

which compound of formula (VI) is:

either, when R'₁ represents a linear or branched ($C_1$–$C_6$) alkoxy group, condensed in the presence of a coupling agent with a hydrazine of formula R—NH—$NH_2$, wherein R is as defined for formula (I), to yield a compound of formula (VII/a)

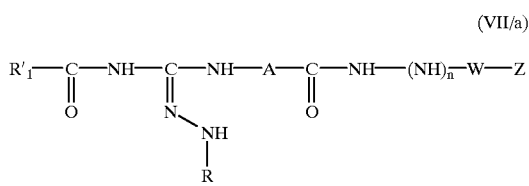

(VII/a)

wherein R, A, n, W and Z are as defined hereinbefore, and R'₁ represents a linear or branched ($C_1$–$C_6$)alkoxy group, which compound (VII/a) cyclises, spontaneously or after treatment in an acid medium, depending upon the nature of the R group to yield a mixture of the two compounds of formulae (I/a) and (I/b):

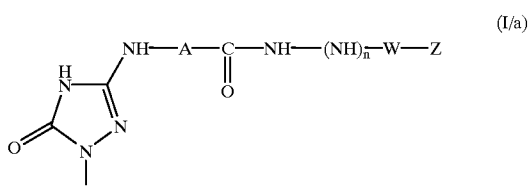

(I/a)

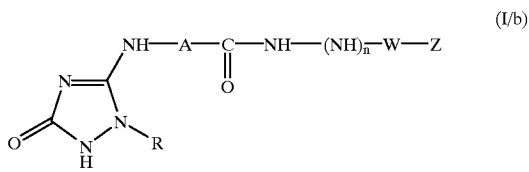

(I/b)

particular cases of the compounds of formula (I) wherein R, A, n, W and Z are as defined hereinbefore, which compounds (I/a) and (I/b) may be separated according to conventional separation techniques, or, when R'₁ represents an R₁ group as defined for formula (I), condensed in the presence of a coupling agent with a hydrazine of formula R—NH—$NH_2$, wherein R is as defined for formula (I), to yield a compound of formula (VII/b)

(VII/b)

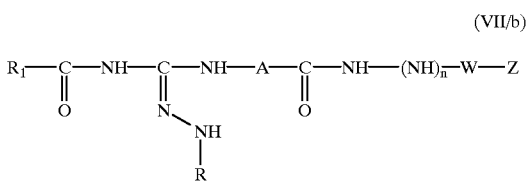

wherein $R_1$, R, A, n, W and Z are as defined hereinbefore, which compound (VII/b) is subjected to a cyclisation reaction followed by dehydration spontaneously or after treatment in an acid medium, depending upon the nature of the R group, to yield a mixture of the two compounds of formulae (I/c) and (I/d):

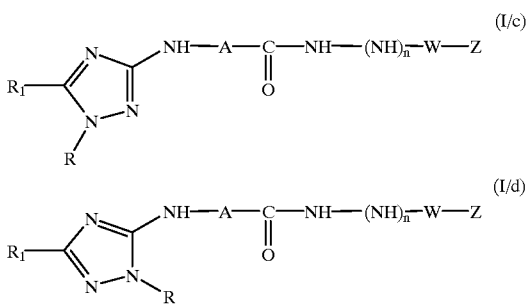

particular cases of the compounds of formula (I) wherein $R_1$, R, A, n, W and Z are as defined hereinbefore, which compounds (I/c) and (I/d) may be separated according to conventional separation techniques, which compounds (I/a), (I/b), (I/c) and (I/d) constitute the totality of the compounds of formula (I), are separated, where appropriate, into their enantiomers and/or diastereoisomers according to a conventional separation technique are converted, if desired, into addition salts thereof with a pharmaceutically acceptable acid or base.

The present invention relates also to pharmaceutical compositions comprising as active ingredient at least one compound of formula (I), on its own or in combination with one or more inert, non-toxic, pharmaceutically acceptable excipients or carriers.

Among the pharmaceutical compositions according to the invention there may be mentioned more especially those that are suitable for oral, parenteral, nasal or transdermal to administration, tablets or dragées, sublingual tablets, gelatin capsules, lozenges, suppositories, creams, ointments, dermal gels, etc. The useful dosage varies according to the age and weight of the patient, the nature and severity of the disorder and the route of administration, which may be oral, nasal, rectal or parenteral. The unit dose generally ranges from 0.05 to 500 mg for a treatment in from 1 to 3 administrations per 24 hours.

The following Examples illustrate the invention and do not limit it in any way. The structures of the compounds described were confirmed by the usual spectroscopic techniques.

The starting materials used are known products or are prepared according to known procedures.

EXAMPLE 1

N'-[4-({5-Phenyl-1-[3-(trifluoromethyl)phenyl]-1H-1,2,4-triazol-3-yl}amino)benzoyl]benzenesulphonohydrazide Step a: Tert-butyl 4-{[2-(phenylsulphonyl)hydrazino]carbonyl}phenylcarbamate 12.1 mmol (1.65 g) of 1-hydroxy-7-azabenzotriazole and 18 mmol (3.45 g) of EDCI are added in succession to a solution of 12 mmol (2.85 g) of 4-[(tert-butoxycarbonyl)amino]benzoic acid in 20 ml of dimethylformamide. The reaction mixture is stirred at room temperature for one hour, and 18 mmol (3.1 g) of benzenesulphonohydrazide are added. After stirring for eight hours at room temperature, the reaction mixture is poured into 100 ml of a 10% hydrochloric acid solution and extracted four times with 50 ml of ethyl acetate. The organic phase is washed twice with 50 ml of water and then three times with an aqueous saturated sodium hydrogen carbonate solution and once with 50 ml of an aqueous saturated sodium chloride solution. After drying over magnesium sulphate, filtration and concentration, the expected product is obtained.

Step b: N'-(4-(Aminobenzoyl)benzenesulphonohydrazide hydrochloride

The compound described in the preceding Step is dissolved in 40 ml of 4M hydrochloric acid in dioxane. After stirring overnight at room temperature, the solvent is removed by evaporation at room temperature. The residue is suspended in 300 ml of ether and filtered. The resulting solid is washed 4 times with 30 ml of ether and then dried under reduced pressure to yield the expected product.

Step c: N-Benzoyl-N'-(4-{[2-phenylsulphonyl)hydrazino]carbonyl}phenyl)thiourea 11.1 mmol (0.66 ml) of diisopropylethylamine are added to a suspension of 11.1 mmol (3.65 g) of the compound described in the preceding Step in 20 ml of acetonitrile. After dissolution, 13.9 mmol (1.86 ml) of benzoyl isothiocyanate are added. The reaction mixture is stirred for 8 hours at room temperature. The precipitate that forms is filtered off and washed twice with 5 ml of acetonitrile and 4 times with 25 ml of ether to yield, after drying, the expected product.

Step d: N'-[4-({5-Phenyl-1-[3-(trifluoromethyl)phenyl]-1H-1,2,4-triazol-3-yl}amino)benzoyl]benzenesulphonohydrazide 3.4 mmol (0.528 ml) of 3-(trifluoromethyl)phenylhydrazine and 6.16 mmol (1.41 g) of EDCI are added to a solution of 3.08 mmol (1.4 g) of the compound described in the preceding Step in 5 ml of dimethylformamide. The reaction mixture is stirred at room temperature overnight. The mixture is poured into 10 ml of aqueous 10% HCl and then extracted 3 times with 100 ml of ethyl acetate. The organic phases are combined and washed once with 20 ml of water, twice with 20 ml of an aqueous saturated sodium hydrogen carbonate solution and once with an aqueous saturated sodium chloride solution. The organic phase is dried over magnesium sulphate, filtered and evaporated. The resulting product is purified by chromatography over silica gel using a dichloromethane/ethyl acetate mixture, 75/25, as eluant to yield the title product.

Mass spectrum: ESI-MS: MH$^+$=579

The compounds of Examples 2 to 25 are obtained according to the process described in Example 1, using the appropriate sulphonohydrazides, isothiocyanates and hydrazines in Steps a, c and d, respectively.

EXAMPLE 2

N'-[4-({5-[2-Chlorophenyl]-1-[3-(trifluoromethyl)phenyl]-1H-1,2,4-triazol-3-yl}amino)benzoyl]benzenesulphonohydrazide Mass spectrum: ESI-MS: MH$^+$=613

EXAMPLE 3

N'-[4-({5-[2-Chlorophenyl]-1-phenyl-1H-1,2,4-triazol-3-yl}amino)benzoyl]benzenesulphonohydrazide Mass spectrum: ESI-MS: MH$^+$=545

EXAMPLE 4

N'-{4-[(1,5-Diphenyl-1H-1,2,4-triazol-3-yl)amino]benzoyl}-4-methoxybenzenesulphonohydrazide

EXAMPLE 5

N'-(4-{[1-(4-Fluorophenyl)-5-phenyl-1H-1,2,4-triazol-3-yl]amino}benzoyl)-4-methoxybenzenesulphonohydrazide

EXAMPLE 6

4-Methoxy-N'-[4-({5-phenyl-1-[3-trifluoromethyl)phenyl]-1H-1,2,4-triazol-3-yl}amino)benzoyl]benzenesulphonohydrazide Mass spectrum: ESI-MS: MH$^+$=609

EXAMPLE 7

N'-(4-{[1-(4-Fluorophenyl)-5-phenyl-1H-1,2,4-triazol-3-yl]amino}benzoyl)-4-methoxybenzenesulphonohydrazide

EXAMPLE 8

N'-{4-[(1,5-Diphenyl-1H-1,2,4-triazol-3-yl)amino]benzoyl}benzenesulphonohydrazide

EXAMPLE 9

N'-[4-({5-[4-Chlorophenyl]-1-[3-(trifluoromethyl)phenyl]-1H-1,2,4-triazol-3-yl}amino)benzoyl]benzenesulphonohydrazide

EXAMPLE 10

N'-(4-{[5-(4-Chlorophenyl)-1-phenyl-1H-1,2,4-triazol-3-yl]amino}benzoyl)benzenesulphonohydrazide Mass spectrum. ESI-MS: MH$^+$=546

EXAMPLE 11

N'-(4-{[5-(4-Chlorophenyl)-1-(4-fluorophenyl)-1H-1,2,4-triazol-3-yl]amino}benzoyl)benzenesulphonohydrazide Mass spectrum: ESI-MS: MH$^+$=564

EXAMPLE 12

N'-[4-({5-[4-Methoxyphenyl]-1-[3-(trifluoromethyl)phenyl]-1H-1,2,4-triazol-3-yl}amino)benzoyl]benzenesulphonohydrazide Mass spectrum: ESI-MS: MH$^+$=609

EXAMPLE 13

N'-(4-{[5-(4-Methoxyphenyl)-1-phenyl-1H-1,2,4-triazol-3-yl]amino}benzoyl)benzenesulphonohydrazide Mass spectrum: ESI-MS: MH$^+$=541

EXAMPLE 14

N'-(4-{[1-(4-Fluorophenyl)-5-(4-methoxyphenyl)-1H-1,2,4-triazol-3-yl]amino}benzoyl)benzenesulphonohydrazide Mass spectrum: ESI-MS: MH$^+$=559

EXAMPLE 15

N'-{4-[(1-Benzyl-5-phenyl-1H-1,2,4-triazol-3-yl)amino]benzoyl}benzenesulphonohydrazide Mass spectrum: ESI-MS: MH$^+$=525

EXAMPLE 16

N'-{4-[(5-Phenyl-1H-1,2,4-triazol-3-yl)amino]benzoyl}benzenesulphonohydrazide

Mass spectrum: ESI-MS: MH$^+$=435

EXAMPLE 17

N'-(4-{[5-Phenyl-1-(2-pyridyl)-1H-1,2,4-triazol-3-yl]amino}benzoyl)benzenesulphonohydrazide Mass spectrum: ESI-MS: MH$^+$=512

EXAMPLE 18

N'-[4-({5-Phenyl-1-[4-(trifluoromethyl)phenyl]-1H-1,2,4-triazol-3-yl}amino)benzoyl]benzenesulphonohydrazide Mass spectrum: ESI-MS: MH$^+$=579

EXAMPLE 19

N'-[4-({5-Phenyl-1-[2-(trifluoromethyl)phenyl]-1H-1,2,4-triazol-3-yl}amino)benzoyl]benzenesulphonohydrazide

EXAMPLE 20

4-Methyl-N'-[4-({5-phenyl-1-[3-(trifluoromethyl)phenyl]-1H-1,2,4-triazol-3-yl}amino)benzoyl]benzenesulphonohydrazide Mass spectrum: ESI-MS: MH$^+$=593

EXAMPLE 21

N'-[4-({5-Phenyl-1-[3-(trifluoromethyl)phenyl]-1H-1,2,4-triazol-3-yl}amino)benzoyl]methanesulphonohydrazide Mass spectrum: ESI-MS: MH$^+$=517

EXAMPLE 22

2,4,6-Trichloro-N'-[4-({5-phenyl-1-[3-(trifluoromethyl)phenyl]-1H-1,2,4-triazol-3-yl}amino)benzoyl]benzenesulphonohydrazide

EXAMPLE 23

2,4,6-Trimethyl-N'-[4-({5-phenyl-1-[3-(trifluoromethyl)phenyl]-1H-1,2,4-triazol1-3-yl}amino)benzoyl]benzenesulphonohydrazide Mass spectrum: ESI-MS: MH$^+$=621

EXAMPLE 24

5-(Dimethylamino)-N'-[4-({5-phenyl-1-[3-(trifluoromethyl)phenyl]-1H-1,2,4-triazol-3-yl}amino)benzoyl]-1-naphthalenesulphonohydrazide Mass spectrum: ESI-MS: MH$^+$=672

EXAMPLE 25

N'-{4-[(1-Benzyl-5-phenyl-1H-1,2,4-triazol-3-yl)amino]benzoyl}-4-methoxysulphonohydrazide Mass spectrum: ESI-MS: MH$^+$=555

EXAMPLE 26

N-[4-({5-Phenyl-1-[3-(trifluoromethyl)phenyl]-1H-1,2,4-triazol-3-yl}amino)benzoyl]benzenesulphonamide The expected product is obtained by using the process described in Example 1, in Step a replacing benzenesulphonohydrazide by benzenesulphonamide.

Mass spectrum ESI-MS: $MH^+$=564

The compounds of Examples 27 and 28 are obtained in the same manner as for Example 26, using the appropriate isothiocyanate and hydrazine in Steps c and d, respectively.

EXAMPLE 27

N-{4-[(1,5-Diphenyl-1H-1,2,4-triazol-3-yl)amino]benzoyl}-benzenesulphonamide

Mass spectrum: ESI-MS: $MH^+$=496

EXAMPLE 28

N-(4-{[1-(4-Fluorophenyl)-5-phenyl-1H-1,2,4-triazol-3-yl]amino}benzoyl)benzenesulphonamide

EXAMPLE 29

N'-[4-({5-Oxo-1-[3-(trifluoromethyl)phenyl]-4,5-dihydro-1H-1,2,4-triazol-3-yl}amino)benzoyl}benzenesulphonohydrazide Step a: Ethyl(4-{[2-(phenylsulphonyl)hydrazino]carbonyl}anilino)carbothioylcarbamate The expected product is obtained according to the process described in Example 1, Step c, replacing benzoyl isothiocyanate by ethyl thioxocarbamate.

Step b: N'-[4-({5-Oxo-1-[3-(trifluoromethyl)phenyl]-4,5-dihydro-1H-1,2,4-triazol-3-yl}amino)benzoyl}benzenesulphonohydrazide 1.065 mmol (0.139 ml) of 3-(trifluoromethyl)phenylhydrazine and 1.42 mmol (0.272 g) of EDCI are added to a solution of 0.71 mmol (0.3 g) of the compound described in the preceding Step in 3 ml of dimethylformamide. The reaction mixture is stirred at room temperature overnight. The mixture is poured into 5 ml of aqueous 10% HCl and then extracted 3 times with 5 ml of ethyl acetate. The organic phases are combined and washed once with 5 ml of water. The organic phase is dried over magnesium sulphate, filtered and evaporated. The residue is taken up in a 10% trifluoroacetic acid solution in dioxane and heated at 50° C. overnight. The reaction mixture is evaporated and the precipitate that forms in the course of the evaporation is washed with 2 ml of acetonitrile and twice with 5 ml of ether and then dried in vacuo to yield the title product.

Mass spectrum: ESI-MS: $MH^+$=519

The compounds of Examples 30 to 39 are obtained according to the process described in Example 29 using the appropriate sulphonohydrazides and hydrazines.

EXAMPLE 30

N'-{4-[(5-Oxo-1-phenyl-4,5-dihydro-1H-1,2,4-triazol-3-yl)amino]benzoyl}benzenesulphonohydrazide Mass spectrum: ESI-MS: $MH^+$=451

EXAMPLE 31

N'-(4-{[1-(4-Fluorophenyl)-5-oxo-4,5-dihydro-1H-1,2,4-triazol-3-yl]amino}benzoyl)benzenesulphonohydrazide Mass spectrum: ESI-MS: $MH^+$=469

EXAMPLE 32

N'-(4-{[5-Oxo-1-(2-pyridyl)-4,5-dihydro-1H-1,2,4-triazol-3-yl]amino}benzoyl)benzenesulphonohydrazide Mass spectrum: ESI-MS: $MH^+$=452

EXAMPLE 33

N'-{4-[(1-Benzyl-5-oxo-4,5-dihydro-1H-1,2,4-triazol-3-yl)amino]benzoyl}benzenesulphonohydrazide

EXAMPLE 34

4-Methyl-N'-[4-({5-oxo-1-[3-(trifluoromethyl)phenyl]-4,5-dihydro-1H-1,2,4-triazol-3-yl}amino)benzoyl]benzenesulphonohydrazide Mass spectrum: ESI-MS: $MH^+$=533

EXAMPLE 35

4-Methoxy-N'-[4-({5-oxo-1-[3-(trifluoromethyl)phenyl]-4,5-dihydro-1H-1,2,4-triazol-3-yl}amino)benzoyl]benzenesulphonohydrazide Mass spectrum: ESI-MS: $MH^+$=549

EXAMPLE 36

4-Methoxy-N'-{4-[(5-oxo-1-phenyl-4,5-dihydro-1H-1,2,4-triazol-3-yl)amino]benzoyl}benzenesulphonohydrazide

EXAMPLE 37

N'-(4-{[1-(4-Fluorophenyl)-5-oxo-4,5-dihydro-1H-1,2,4-triazol-3-yl]amino}benzoyl)-4-methoxybenzenesulphonohydrazide

EXAMPLE 38

N'-{4-[(1-Benzyl-5-oxo-4,5-dihydro-1H-1,2,4-triazol-3-yl)amino]benzoyl}-4-methoxybenzenesulphonohydrazide

EXAMPLE 39

N'-Benzoyl-4-({5-phenyl-1-[3-(trifluoromethyl)phenyl]-1H-1,2,4-triazol-3-yl}amino)benzohydrazide The expected product is obtained according to the process described in Example 1 in Step a replacing benzenesulphonohydrazide by benzohydrazide.

Mass spectrum: ESI-MS: $MH^+$=543

The compounds of Examples 40 to 45 are obtained in the same manner as for Example 39, replacing sulphonohydrazide by the corresponding hydrazide and using the appropriate isothiocyanates and hydrazines.

EXAMPLE 40

N'-Benzoyl-4-[(1,5-diphenyl-1H-1,2,4-triazol-3-yl)amino]benzohydrazide

Mass spectrum: ESI-MS: $MH^+$=475

EXAMPLE 41

N'-Benzoyl-4-{[1-(4-fluorophenyl)-5-phenyl-1H-1,2,4-triazol-3-yl]amino}benzohydrazide Mass spectrum: ESI-MS: $MH^+$=493

EXAMPLE 42

N'-Benzoyl-4-{[5-phenyl-1-(2-pyridyl)-1H-1,2,4-triazol-3-yl]amino}benzohydrazide Mass spectrum: ESI-MS: MH$^+$=476

EXAMPLE 43

N'-Benzoyl-4-({1-[3,5-bis(trifluoromethyl)phenyl]-5-phenyl-1H-1,2,4-triazol-3-yl}amino)benzohydrazide Mass spectrum: ESI-MS: MH$^+$=611

EXAMPLE 44

4-[(1,5-Diphenyl-1H-1,2,4-triazol-3-yl)amino]-N'-(1-naphthoyl)benzohydrazide

Mass spectrum ESI-MS: MH$^+$=525

EXAMPLE 45

4-{[1-(4-Fluorophenyl)-5-phenyl-1H-1,2,4-triazol-3-yl]amino}-N'-(1-naphthoyl)benzohydrazide Mass spectrum: ESI-MS: MH$^+$=543

The compounds of Examples 46 to 48 are obtained according to the process described in Example 1, using the appropriate sulphonohydrazides, isothiocyanates and hydrazines in Steps a, c and d, respectively.

EXAMPLE 46

4-Methyl-N'-{4-[(5-phenyl)-1H-1,2,4-triazol-3-yl)amino]benzoyl}benzenesulphonohydrazide Mass spectrum: ESI-MS: MH$^+$=449

EXAMPLE 47

N'-{4-[(5-Phenyl)-1H-1,2,4-triazol-3-yl)amino]benzoyl}methanesulphonohydrazide

Mass spectrum: ESI-MS: MH$^+$=373

EXAMPLE 48

4-Methoxy-N'-{4-[(5-phenyl-1H-1,2,4-triazol-3-yl)amino]benzoyl}benzenesulphonohydrazide The compounds of Examples 49 to 60 are obtained according to the process described in Example 1, using the appropriate sulphonohydrazides, isothiocyanates and hydrazines in Steps a, c and d, respectively, and in Step a replacing 4-[(tert-butoxycarbonyl)amino]benzoic acid by 3-[(tert-butoxycarbonyl)amino]benzoic acid.

EXAMPLE 49

N'-[3-({5-Phenyl-1-[3-(trifluoromethyl)phenyl]-1H-1,2,4-triazol-3-yl}amino)benzoyl]benzenesulphonohydrazide Mass spectrum: ESI-MS: MH$^+$=579

EXAMPLE 50

N'-{3-[(1,5-Diphenyl-1H-1,2,4-triazol-3-yl)amino]benzoyl}benzenesulphonohydrazide Mass spectrum: ESI-MS: MH$^+$=511

EXAMPLE 51

N'-(3-{[5-Phenyl-1-(2-pyridinyl)-1H-1,2,4-triazol-3-yl]amino}benzoyl)benzenesulphonohydrazide Mass spectrum: ESI-MS: MH$^+$=512

EXAMPLE 52

N'-(3-{[5-(2-Chlorophenyl)-1-phenyl-1H-1,2,4-triazol-3-yl]amino}benzoyl)benzenesulphonohydrazide Mass spectrum: ESI-MS: MH$^+$=546

EXAMPLE 53

N'-(3-{[5-(2-Chlorophenyl)-1-(2-pyridinyl)-1H-1,2,4-triazol-3-yl]amino}benzoyl)benzenesulphonohydrazide Mass spectrum ESI-MS: MH$^+$=547

EXAMPLE 54

4-Methoxy-N'-[3-({5-phenyl-1-[3-(trifluoromethyl)phenyl]-1H-1,2,4-triazol-3-yl}amino)benzoyl]benzenesulphonohydrazide Mass spectrum: ESI-MS: MH$^+$=609

EXAMPLE 55

N'-{3-[(1,5-Diphenyl-1H-1,2,4-triazol-3-yl)amino]benzoyl}-4-methoxybenzenesulphonohydrazide Mass spectrum: ESI-MS: MH$^+$=541

EXAMPLE 56

4-Methoxy-N'-(3-{[5-phenyl-1-(2-pyridinyl)-1H-1,2,4-triazol-3-yl]amino}benzoyl)benzenesulphonohydrazide Mass spectrum: ESI-MS: MH$^+$=542

EXAMPLE 57

N'-[3-({5-(2-Chlorophenyl)-1-[3-(trifluoromethyl)phenyl]-1H-1,2,4-triazol-3-yl}amino)benzoyl]-4-methoxybenzenesulphonohydrazide Mass spectrum: ESI-MS: MH$^+$=644

EXAMPLE 58

N'-(3-{5-(2-Chlorophenyl)-1-phenyl-1H-1,2,4-triazol-3-yl]amino}benzoyl)-4-methoxybenzenesulphonohydrazide Mass spectrum: ESI-MS: MH$^+$=576

EXAMPLE 59

N'-(3-({[5-(2-Chlorophenyl)-1-(2-pyridinyl)-1H-1,2,4-triazol-3-yl]amino}benzoyl)-4-methoxybenzenesulphonohydrazide Mass spectrum: ESI-MS: MH$^+$=577

EXAMPLE 60

N'-[3-({5-(2-Chlorophenyl)-1-[3-(trifluoromethyl)phenyl]-1H-1,2,4-triazol-3-yl}amino)benzoyl]benzenesulphonohydrazide Mass spectrum: ESI-MS: MH$^+$=614

The compounds of Examples 61 to 63 are obtained according to the process described in Example 1, using the appropriate sulphonohydrazides, isothiocyanates and hydrazines in Steps a, c and d, respectively, and in Step a replacing 4-[(tert-butoxycarbonyl)amino]benzoic acid by 4-{[(tert-butoxycarbonyl)amino]methyl}benzoic acid.

EXAMPLE 61

4-Methoxy-N'-{4-[({5-phenyl-1-[3-(trifluoromethyl) phenyl]-1H-1,2,4-triazol-3-yl}amino)methyl] benzoyl}benzenesulphonohydrazide Mass spectrum: ESI-MS: MH$^+$=737

EXAMPLE 62

N'-(4-{[(1,5-Diphenyl-1H-1,2,4-triazol-3-yl)amino] methyl}benzoyl)benzenesulphonohydrazide Mass spectrum: ESI-MS: MH$^+$=639

EXAMPLE 63

N'-[4-({[5-Phenyl-1-(2-pyridinyl)-1H-1,2,4-triazol-3-yl]amino}methyl)benzoyl] benzenesulphonohydrazide Mass spectrum: ESI-MS: MH$^+$=754

The compounds of Examples 64 to 66 are obtained according to the process described in Example 1, using the appropriate sulphonohydrazides, isothiocyanates and hydrazines in Steps a, c and d, respectively, and in Step a replacing 4-[(tert-butoxycarbonyl)amino]benzoic acid by {4-[(tert-butoxycarbonyl)amino]phenyl}acetic acid.

EXAMPLE 64

4-Methoxy-N'-{[4-({5-phenyl-1-[3-(trifluoromethyl) phenyl]-1H-1,2,4-triazol-3-yl}amino)phenyl] acetyl}benzenesulphonohydrazide Mass spectrum: ESI-MS: MH$^+$=623

EXAMPLE 65

N'-({4-[1(1,5-Diphenyl-1H-1,2,4-triazol-3-yl)amino] phenyl}acetyl)-4-methoxybenzenesulphonohydrazide Mass spectrum: ESI-MS: MH$^+$=555

EXAMPLE 66

4-Methoxy-N'-[(4-{[5-phenyl-1-(2-pyridinyl)-1H-1, 2,4-triazol-3-yl]amino}phenyl)acetyl] benzenesulphonohydrazide Mass spectrum: ESI-MS: MH$^+$=556

The compounds of Examples 67 to 72 are obtained according to the process described in Example 1 using the appropriate sulphonohydrazides, isothiocyanates and hydrazines in Steps a, c and d respectively, and in Step a replacing 4-[(tert-butoxycarbonyl)amino]benzoic acid by 6-[(tert-butoxycarbonyl)amino]-3-pyridazinecarboxylic acid.

EXAMPLE 67

4-Methoxy-N'-{[6-({5-phenyl-1-[3-(trifluoromethyl) phenyl]-1H-1,2,4-triazol-3-yl}amino)-3-pyridazinyl] carbonyl}benzenesulphonohydrazide Mass spectrum: ESI-MS: MH$^+$=611

EXAMPLE 68

N'-({6-[1(1,5-Diphenyl-1H-1,2,4-triazol-3-yl) amino]-3-pyridazinyl}carbonyl)-4-methoxybenzenesulphonohydrazide Mass spectrum: ESI-MS: MH$^+$=543

EXAMPLE 69

4-Methoxy-N'-[(6-{[5-phenyl-1-(2-pyridinyl)-1H-1, 2,4-triazol-3-yl]amino}-3-pyridazinyl)carbonyl] benzenesulphonohydrazide Mass spectrum: ESI-MS: MH$^+$=544

EXAMPLE 70

N'-{[6-({5-Phenyl-1-[3-(trifluoromethyl)phenyl]-1H-1,2,4-triazol-3-yl}amino)-3-pyridazinyl] carbonyl}benzenesulphonohydrazide Mass spectrum: ESI-MS: MH$^+$=581

EXAMPLE 71

N'-({6-[(1,5-Diphenyl-1H-1,2,4-triazol-3-yl)amino]-3-pyridazinyl}carbonyl)benzenesulphonohydrazide Mass spectrum: ESI-MS: MH$^+$=513

EXAMPLE 72

N'-[(6-{[5-Phenyl-1-(2-pyridinyl)-1H-1,2,4-triazol-3-yl]amino}-3-pyridazinyl)carbonyl] benzenesulphonohydrazide Mass spectrum: ESI-MS: MH$^+$=514

The compounds of Examples 73 to 75 are obtained according to the process described in Example 1 using the appropriate sulphonohydrazides, isothiocyanates and hydrazines in Steps a, c and d, respectively, and in Step a replacing 4-[(tert-butoxycarbonyl)amino]benzoic acid by 6-[(tert-butoxycarbonyl)amino]nicotinic acid.

EXAMPLE 73

N'-{[6-({5-Phenyl-1-[3-(trifluoromethyl)phenyl]-1H-1,2,4-triazol-3-yl}amino)-3-pyridinyl] carbonyl}benzenesulphonohydrazide Mass spectrum: ESI-MS: MH$^+$=580

EXAMPLE 74

N'-({6-[(1,5-Diphenyl-1H-1,2,4-triazol-3-yl)amino]-3-pyridinyl}carbonyl)benzenesulphonohydrazide Mass spectrum: ESI-MS: MH$^+$=512

EXAMPLE 75

N'-[(6-{[5-Phenyl-1-(2-pyridinyl)-1H-1,2,4-triazol-3-yl]amino}-3-pyridinyl)carbonyl] benzenesulphonohydrazide Mass spectrum: ESI-MS: MH$^+$=513

The compounds of Examples 76 to 78 are obtained according to the process described in Example 1 using the appropriate sulphonohydrazides and hydrazines.

EXAMPLE 76

4-Methyl-N'-[4-({5-oxo-1-[3-(trifluoromethyl) phenyl]-4,5-dihydro-1H-1,2,4-triazol-3-yl}amino) benzoyl]benzenesulphonohydrazide Mass spectrum: ESI-MS: MH$^+$=533

EXAMPLE 77

2,4,6-Trimethyl-N'-[4-({5-oxo-1-[3-(trifluoromethyl)
phenyl]-4,5-dihydro-1H-1,2,4-triazol-3-yl}amino)
benzoyl]benzenesulphonohydrazide Mass spectrum: ESI-MS: MH$^+$=561

EXAMPLE 78

N'-[4-({5-Oxo-1-[3-(trifluoromethyl)phenyl]-4,5-
dihydro-1H-1,2,4-triazol-3-yl]amino)benzoyl]
methanesulphonohydrazide Mass spectrum: ESI-MS: MH$^+$=457

EXAMPLE 79

N'-[(6-{[5-Oxo-1-(2-pyridinyl)-4,5-dihydro-1H-1,2,
4-triazol-3-yl]amino}-3-pyridinyl)carbonyl]
benzenesulphonohydrazide The expected product is obtained according to the process described in Example 1, Steps a, b and c, in Step a replacing 4-[(tert-butoxycarbonyl)amino]benzoic acid by 6-[(tert-butoxycarbonyl)amino]nicotinic acid, in Step c replacing benzoyl isothiocyanate by ethyl thioxocarbamate, and, according to the process described in Example 21, Step b, replacing 3-(trifluoromethyl)phenylhydrazine by 2-hydrazinopyridine.

Mass spectrum: ESI-MS: MH$^+$=453

The products of Examples 80 to 96 are obtained according to the process described in Example 1, in Step a replacing the sulphonohydrazides by the appropriate hydrazides, and using the appropriate isothiocyanates and hydrazines in Steps c and d, respectively.

EXAMPLE 80

4-[(1,5-Diphenyl-1H-1,2,4-triazol-3-yl)amino]-N'-
(3-nitrobenzoyl)benzohydrazide Mass spectrum: ESI-MS: MH$^+$=520

EXAMPLE 81

4-[1(1,5-Diphenyl-1H-1,2,4-triazol-3-yl)amino]-N'-
[4-(trifluoromethyl)benzoyl]benzohydrazide Mass spectrum: ESI-MS: MH$^+$=543

EXAMPLE 82

4-[(1,5-Diphenyl-1H-1,2,4-triazol-3-yl)amino]-N'-
(3,4,5-trimethoxybenzoyl)benzohydrazide Mass spectrum: ESI-MS: MH$^+$=565

EXAMPLE 83

4-[(1,5-Diphenyl-1H-1,2,4-triazol-3-yl)amino]-N'-
(3-methoxybenzoyl)benzohydrazide Mass spectrum: ESI-MS: MH$^+$=505

EXAMPLE 84

4-[(1,5-Diphenyl-1H-1,2,4-triazol-3-yl)amino]-N'-
(4-methoxybenzoyl)benzohydrazide Mass spectrum: ESI-MS: MH$^+$=505

EXAMPLE 85

4-[(1,5-Diphenyl-1H-1,2,4-triazol-3-yl)amino]-N'-
(3-furoyl)benzohydrazide

Mass spectrum: ESI-MS: MH$^+$=465

EXAMPLE 86

4-[(1,5-Diphenyl-1H-1,2,4-triazol-3-yl)amino]-N'-
isonicotinoylbenzohydrazide

Mass spectrum: ESI-MS: MH$^+$=476

EXAMPLE 87

4-[(1,5-Diphenyl-1H-1,2,4-triazol-3-yl)amino]-N'-
(1-naphthoyl)benzohydrazide

Mass spectrum: ESI-MS: MH$^+$=539

EXAMPLE 88

N'-(3,4-Dimethoxybenzoyl)-4-[(1,5-diphenyl-1H-1,
2,4-triazol-3-yl)amino]benzohydrazide Mass spectrum: ESI-MS: MH$^+$=535

EXAMPLE 89

4-[(1,5-Diphenyl-1H-1,2,4-triazol-3-yl)amino]-N'-
(2-naphthoyl)benzohydrazide

Mass spectrum: ESI-MS: MH$^+$=525

EXAMPLE 90

N'-(3-Chlorobenzoyl)-4-[(1,5-diphenyl-1H-1,2,4-
triazol-3-yl)amino]benzohydrazide Mass spectrum: ESI-MS: MH$^+$=509

EXAMPLE 91

N'-[3,5-Bis(trifluoromethyl)benzoyl]-4-[(1,5-
diphenyl-1H-1,2,4-triazol-3-yl)amino]
benzohydrazide Mass spectrum: ESI-MS: MH$^+$=611

EXAMPLE 92

4-[(1,5-Diphenyl-1H-1,2,4-triazol-3-yl)amino]-N'-
(2-thienylcarbonyl)benzohydrazide Mass spectrum: ESI-MS: MH$^+$=481

EXAMPLE 93

N'-(4-Chlorobenzoyl)-4-[(1,5-diphenyl-1H-1,2,4-
triazol-3-yl)amino]benzohydrazide Mass spectrum: ESI-MS: MH$^+$=509

EXAMPLE 94

N'-(2-Chlorobenzoyl)-4-[(1,5-diphenyl-1H-1,2,4-
triazol-3-yl)amino]benzohydrazide Mass spectrum: ESI-MS: MH$^+$=509

EXAMPLE 95

4-[(1,5-Diphenyl-1H-1,2,4-triazol-3-yl)amino]-N'-
(3-hydroxybenzoyl)benzohydrazide Mass spectrum: ESI-MS: MH$^+$=491

EXAMPLE 96

4-[(1,5-Diphenyl-1H-1,2,4-triazol-3-yl)amino]-N'-
(3,4,5-trihydroxybenzoyl)benzohydrazide Mass spectrum: ESI-MS: MH$^+$=523

EXAMPLE 97

N'-{4-[(1-Benzyl-3-phenyl-1H-1,2,4-triazol-5-yl)amino]benzoyl}benzenesulfonohydrazide The title product isolated during the purification of the compound described in example 15.

EXAMPLE 98

N'-{4-[(1-Benzyl-3-phenyl-1H-1,2,4-triazol-5-yl)amino]benzoyl}-4-méthoxybenzenesulfonohydrazide The title product isolated during the purification of the compound described in example 25.

Pharmacological Study

EXAMPLE A

Measurement of the Effect on Food Intake and Weight Development in the Obese Mouse The compounds of the invention were administered in vivo to the obese ob/ob mouse in order to evaluate their influence on food intake and weight development. The animals used are 13- to 18-week-old female ob/ob C57B1/6J mice. They are divided into groups each comprising 4 animals per cage, the cages being fitted with a grating floor, and the mice having free access to food.

Before the experiments, the animals are conditioned for a period ranging from 2 to 3 weeks until their food consumption has stabilised. The experiments may be summarised as follows:

D−14 to D−7: conditioning
D=7 to D−3: measurement of the basal food intake
D0 to D+3: animals treated twice daily, the control groups being given the carrier
D0 to D+4: daily measurement of food intake and body weight.

The test compounds are dissolved, immediately before use, in water, 0.9% sodium chloride, propylene glycol or dimethyl sulphoxide, depending upon their solubility, and are administered intraperitoneally (IP), in a volume of 2.5 ml/kg.

The parameters measured are the food intake and the body weight.

Results

The results are expressed as
percentage variation in food intake under treatment compared with the basal food intake;
percentage variation in body weight between the first and last day of treatment.

By way of example, the results obtained with the compounds of Examples 1 and 6 are as follows

| Product | Dose (mg/kg) | Food intake % variation (D1) Control | Food intake % variation (D1) Treated | Body weight % variation (D4/D0) |
|---|---|---|---|---|
| Example 1 | 1 | −34 | −45 | −6.4 |
| Example 6 | 5 | −23 | −34 | −11.2 |

EXAMPLE B

Meaurement of the in vitro Affinity for NPY Receptors

The capacity of the compounds of the invention to bind to NPY receptors was measured on various cell lines, each expressing one of the receptor sub-types studied. Competition binding experiments were carried out using the peptide [$^{125}$I]-PYY as radioligand at concentrations ranging from 15 to 65 pM. The non-specific fraction is measured in the presence of a concentration of 1 μM NPY. The cells are incubated for a period ranging from 1 to 2 hours depending upon the lines, and the radioactivity is collected after filtration over a GF/C filter treated with 0.1% PEI, before being measured.

Results

The results are expressed as $IC_{50}$. The compounds of the invention appear to be capable of significantly displacing the reference ligand: the $IC_{50}$ values vary from a few nanomoles to some hundreds of nanomoles.

By way of example, the compounds of Examples 1 and 6 have an $IC_{50}$ value of 80 nM and 7 nM, respectively, for the $Y_5$ receptor.

EXAMPLE C

Acute Toxicity Study

Acute toxicity was evaluated after oral administration of increasing doses of the test compound to groups each comprising 8 mice (26±6 grams). The animals were observed at regular intervals over the course of the first day and daily for the two weeks following treatment. The compounds of the invention appear to be not very toxic at all.

EXAMPLE D

Pharmaceutical Composition

Formulation for the preparation of 1000 tablets each comprising a dose of 10 mg

| | |
|---|---|
| Compound of Example | 110 g |
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I):

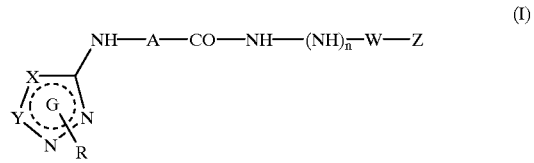

(I)

wherein:

n is 0 or 1,

W represents —CO— or $S(O)_q$ wherein q is 0, 1 or 2,

represents a group selected from:

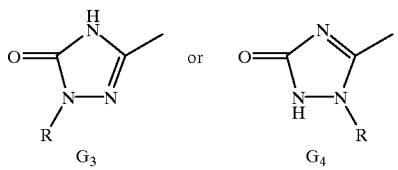

Z represents alkyl, optionally substituted aryl, optionally substituted arylalkyl, optionally substituted arylalkenyl, or optionally substituted arylalkynyl, A represents a grouping selected from —A$_2$—, —A$_1$—A$_2$—, —A$_2$—A$_1$—, and —A$_1$—A$_2$—A$_1$—, wherein A$_1$ is alkylene and A$_2$ represents optionally substituted phenylene, optionally substituted naphthylene, or cycloalkylene, R represents hydrogen, alkyl, optionally substituted aryl, optionally substituted arylalkyl, optionally substituted arylalkenyl, or optionally substituted arylalkynyl, their enantiomers, diastereoisomers, or addition salt thereof with a pharmaceutically-acceptable acid or base, it being understood that the term "alkyl" denotes linear or branched alkyl having 1 to 6 carbon atoms, the term "alkylene" denotes linear or branched alkylene having 1 to 6 carbon atoms, the term "alkenyl" denotes linear or branched alkenyl having 2 to 6 carbon atoms and 1 to 3 double bonds, the term "alkynyl" denotes linear or branched alkynyl having 2 to 6 carbon atoms and 1 to 3 triple bonds, the term "aryl" denotes phenyl, naphthyl, biphenyl, dihydronaphthyl, or tetrahydronaphthyl, the terms "phenylene" and "naphthylene" denote bivalent phenyl and naphthyl radicals, the term cycloalkylene denotes a bivalent saturated cyclic radical having 3 to 8 carbon atoms, the expression "optionally substituted" applied to the terms "aryl" and "arylalkyl", means that those groups are substituted on their cyclic moiety by 1 to 5 identical or different substituents selected from linear or branched (C$_1$–C$_6$)alkyl, linear or branched (C$_1$–C$_6$)alkoxy, halogen, hydroxy, linear or branched perhalo-(C$_1$–C$_6$)alkyl, nitro, amino (optionally substituted by one or two linear or branched (C$_1$–C$_6$)alkyl), linear or branched (C$_1$–C$_6$)acyl, aminocarbonyl (optionally substituted on the nitrogen atom by one or two linear or branched (C$_1$–C$_6$)alkyl), linear or branched (C$_1$–C$_6$) acylamino, linear or branched (C$_1$–C$_6$)alkoxycarbonyl, formyl, carboxy, sulpho, nitrile, linear or branched (C$_1$–C$_6$) aminoalkyl (optionally substituted on the nitrogen atom by one or two linear or branched (C$_1$–C$_6$)alkyl), or linear or branched (C$_1$–C$_6$)hydroxyalkyl (optionally substituted on the oxygen atom by a linear or branched (C$_1$–C$_6$)alkyl), and the expression "optionally substituted" applied to the terms "phenylene" or "naphthylene" means that those groups are substituted by one to three identical or different groups selected from linear or branched (C$_1$–C$_6$)alkyl, linear or branched (C$_1$–C$_6$)alkoxy, halogen, hydroxy, linear or branched perhalo-(C$_1$–C$_6$)alkyl, nitro, amino (optionally substituted by one or two linear or branched (C$_1$–C$_6$)alkyl, linear or branched (C$_1$–C$_6$)acyl, formyl, carboxy, linear or branched (C$_1$–C$_6$)alkoxycarbonyl, aminocarbonyl (optionally substituted on the nitrogen atom by one or two linear or branched (C$_1$–C$_6$)alkyl, linear or branched (C$_1$–C$_6$) acylamino, and nitrile.

2. A compound of claim 1 wherein n is 1.

3. A compound of claim 1 wherein n is 0.

4. A compound of claim 1 wherein W represents SO$_2$.

5. A compound of claim 1 wherein

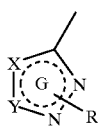

represents a group selected from:

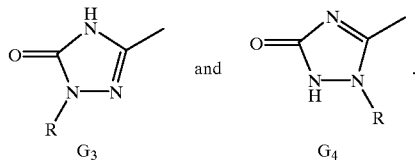

6. A compound of claim 1 wherein A represents A$_2$.

7. A compound of formula (I) according to claim 1 wherein A represents —A$_1$—A$_2$— or —A$_2$—A$_1$—.

8. A compound of claim 1 wherein R$_1$ represents optionally substituted aryl.

9. A compound of claim 1 wherein R is selected from hydrogen and optionally substituted aryl.

10. A compound of claim 1 wherein Z represents a group selected from alkyl and optionally substituted aryl.

11. A compound of claim 1 wherein n is 1, W represents SO$_2$, A represents a group selected from phenylene, R$_1$ represents optionally substituted aryl, R is selected from hydrogen and optionally substituted aryl, and Z represents alkyl or optionally substituted aryl.

12. Compound of claim 1 which is N'-(4-({5-oxo-1-[3-(trifluoromethyl)phenyl]-4,5-dihydro-1H-1,2,4-triazol-3-yl}amino)benzoyl}benzene-sulphonohydrazide.

13. A pharmaceutical composition useful as a Neuropeptide Y receptor ligand comprising as active principle an effective amount of a compound as claimed in claim 1 together with one or more pharmaceutically-acceptable excipients or vehicles.

* * * * *

UNITED STATES PATENT AND TRADEMARK OFFICE
CERTIFICATE OF CORRECTION

PATENT NO. : 6,245,916 B1
DATED : June 12, 2001
INVENTOR(S) : Jean-Luc Fauchere et al.

It is certified that error appears in the above-identified patent and that said Letters Patent is hereby corrected as shown below:

<u>Title page,</u>
Iten [57], ABSTRACT,
Line 26, "heteroarylakenyl" should read -- heteroarylalkenyl --
Line 27, "heteroarylalkenyl" should read -- heteroarylalkyl --
Line 28, "heteroary" should read -- heteroaryl --

<u>Column 21,</u>
Line 35, the line "phenyl and naphthyl radical," should read -- phenyl and naphthyl radicals, respectively, --
Line 51, after "($C_1$-$C_6$)alkyl),: please insert linear or branched ($C_1$-$C_6$)thioalkyl (optionally substituted on the sulfur atom by a linear or branced ($C_1$-$C_6$)alkyl), --

<u>Column 22,</u>
Line 34, after the words "A compound of" please delete -- formula (I) according to --
Line 46, "(4" should read -- {4 --

Signed and Sealed this

Twenty-seventh Day of August, 2002

*Attest:*

JAMES E. ROGAN
*Attesting Officer*   *Director of the United States Patent and Trademark Office*